United States Patent
Kirst et al.

(10) Patent No.: US 9,850,481 B2
(45) Date of Patent: *Dec. 26, 2017

(54) METHOD FOR GENOME COMPLEXITY REDUCTION AND POLYMORPHISM DETECTION

(71) Applicant: University of Florida Research Foundation, Inc., Gainesville, FL (US)

(72) Inventors: Matias Kirst, Gainesville, FL (US); Marcio Fernando Ribeiro De Resende, Jr., Gainesville, FL (US); Leandro Gomide Neves, Gainesville, FL (US); Christopher Dervinis, High Springs, FL (US); Kelly Mayrink Balmant, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 200 days.

This patent is subject to a terminal disclaimer.

(21) Appl. No.: 14/553,053

(22) Filed: Nov. 25, 2014

(65) Prior Publication Data

US 2015/0133316 A1 May 14, 2015

Related U.S. Application Data

(63) Continuation of application No. 13/535,190, filed on Jun. 27, 2012, now Pat. No. 8,921,076.

(60) Provisional application No. 61/571,472, filed on Jun. 27, 2011, provisional application No. 61/555,711, filed on Nov. 4, 2011.

(51) Int. Cl.
  *C12P 19/34* (2006.01)
  *C12N 15/10* (2006.01)
  *C12Q 1/68* (2006.01)

(52) U.S. Cl.
  CPC ....... *C12N 15/1065* (2013.01); *C12Q 1/6806* (2013.01); *C12Q 1/6853* (2013.01); *C12Q 1/6874* (2013.01)

(58) Field of Classification Search
  CPC ........ C12Q 2521/301; C12Q 2525/155; C12Q 2525/161; C12Q 2525/179; C12Q 2535/122; C12Q 2537/159; C12Q 2563/179; C12Q 1/6806; C12Q 1/6853; C12Q 1/6874; C12N 15/1065
  USPC ........................................................ 435/91.2
  See application file for complete search history.

(56) References Cited

U.S. PATENT DOCUMENTS 8,921,076 B2 * 12/2014 Kirst .................... C12Q 1/6806
                                                               435/91.2
2009/0036323 A1   2/2009 Van Eijk et al.
2009/0220955 A1   9/2009 Verrant
2010/0092976 A1   4/2010 Hirakawa et al.
2011/0105364 A1   5/2011 Kurn

FOREIGN PATENT DOCUMENTS

WO   WO 2010/127186   11/2010

OTHER PUBLICATIONS

Cheung et al., "Whole genome amplification using a degenerate oligonucleotide primer allows hundreds of genotypes to be performed on less than one nanogram of genomic DNA," *PNAS USA* 93(25):14676-14679, 1996.
Christodoulou et al., "Construction of normalized RNA-seq libraries for next-generation sequencing using the crab duplex-specific nuclease," *Curr Prot Molec Biol* Chapter 4, unit 4.12, Apr. 2011.
Davey et al., "Genome-wide marker discovery and genotyping using next-generation sequencing," *Nat Rev Genet* 12(7):499-510, 2011.
Fu et al., "Repeat subtraction-mediated sequence capture from a complex genome," *Plant J* 62(5):898-909, 2010.
Galindo et al., "An EST-based genome scan using 454 sequencing in the marine snail *Littorina saxatilis*," *J Evol Biol* 23(9):2004-2016, 2010.
Jordan et al., "Genome complexity reduction for SNP genotyping analysis," *PNAS USA* 99:2942-2947, 2002.
Karatolos et al., "Pyrosequencing the transcriptome of the greenhouse whitefly, *Trialeurodes vaporariorum* reveals multiple transcripts encoding insecticide targets and detoxifying enzymes," *BMC Genet* 12:56, 2011.
Kirst, Presentation entitled "Rapid Genomics, a DNA genotyping and data analysis company," RAPiD Genomics, Gainesville, FL., Feb. 2012.
McKenna et al., Poster, Iowa State University, "A simple method to reduce genome complexity for genotyping by sequencing," <http://www.reu.iastate.edu/2011/Projects%20for%20web%20posting/6%20McKenna-.
Peterson et al., Chapter 13, "Reduced representation strategies and their application to plant genomes," in: "The Handbook of Plant Genome Mapping, Genetic and Physical Mapping," Meksem and Kahl, eds., 2005.
Shagin et al., "A Novel Method for SNP Detection Using a New Duplex-Specific Nuclease From Crab Hepatopancreas," *Genome Res* 12:1935-42, 2002.
Williams et al., SNP identification, verification, and utility for population genetics in a non-model genus, *BMC Genet* 11:32, 2010.
Zhulidov et al., "Simple cDNA normalization using kamchatka crab duplex-specific nuclease," *Nucleic Acids Res* 32(3):e37, 2004.

(Continued)

*Primary Examiner* — Cynthia B Wilder
(74) *Attorney, Agent, or Firm* — Dentons US LLP

(57) ABSTRACT

The present invention provides methods to produce a reduced representation of a genome for sequencing and DNA polymorphism detection. In particular, the invention provides PCR-based methods, with normalization of the amplified products using a duplex-specific nuclease, in order to reduce over-representation of PCR products. Oligonucleotides for use in the disclosed method are also provided.

36 Claims, 6 Drawing Sheets

(56) References Cited

OTHER PUBLICATIONS

"Notification of Transmittal of the International Search Report and the Written Opinion of the International Searching Authority, or the Declaration," for PCT/US2012/044444, dated Jan. 23, 2013.

Bogdanova et al., "Normalizing cDNA Libraries," *Current Protocols in Molecular Biology* 90(5.12):5.12.1-5.12.27, 2010.

Bogdanova et al., "Normalization of full-length-enriched cDNA," Ch. 6 in: cDNA Libraries: Methods and Applications. vol. 729 of Methods in Molecular Biology. Chaofu Lu et al. (eds.). pp. 89-98, 2011.

Peng et al., "Kamchatka crab duplex-specific nuclease-mediated transcriptome subtraction method for identifying long cDNAs of differentially expressed genes," *Analytical Biochemistry* 372:148-155, 2008.

European Search Report regarding European Patent Application No. 12 804 156.3, dated Jan. 26, 2015.

\* cited by examiner

```
AATGATACGGCGACCACCGAGATCTACACTCTTTCCCTACACGACGCTCTTCCGATCT
                              ||||||||||||||||||||||||
                              TGTGCTGCGAGAAGGCTAGATGACNNNNNNNNNNNGAGCGG <FRAG>
degenerate oligonucleotide primer ⟶ ACACGACGCTCTTCCGATCTACTGNNNNNNNNNNNCTCGCC <FRAG>
```

FIG.5

SEQUENCE LISTING

```
<160> NUMBER OF SEQ ID NOS: 29

<210> SEQ ID NO 1
<211> LENGTH: 25
<212> TYPE: DNA
<213> ORGANISM: Artificial sequence
<220> FEATURE:
<223> OTHER INFORMATION: Primer

<400> SEQUENCE: 1
aatgatacgg cgaccaccga gatct                                        25

<210> SEQ ID NO 2
<211> LENGTH: 33
<212> TYPE: DNA
<213> ORGANISM: Artificial sequence
<220> FEATURE:
<223> OTHER INFORMATION: Primer

<400> SEQUENCE: 2
acactctttc cctacacgac gctcttccga tct                               33

<210> SEQ ID NO 3
<211> LENGTH: 58
<212> TYPE: DNA
<213> ORGANISM: Artificial sequence
<220> FEATURE:
<223> OTHER INFORMATION: Primer

<400> SEQUENCE: 3
aatgatacgg cgaccaccga gatctacact ctttccctac acgacgctct tccgatct    58

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
acacgacgct cttccgatct                                              20

<210> SEQ ID NO 5
<211> LENGTH: 40
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (25)..(34)
<223> OTHER INFORMATION: n is a, c, g, or t
```

<400> SEQUENCE: 5
acacgacgct cttccgatct actgnnnnnn nnnnctcgcc    40

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
acacgacgct cttccgatct    20

<210> SEQ ID NO 7
<211> LENGTH: 36
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(30)
<223> OTHER INFORMATION: n is a, c, g, or t

<400> SEQUENCE: 7
ctgaacccTT gtcgccattc nnnnnnnnnn cctccg    36

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
acacgacgct cttccgatct    20

<210> SEQ ID NO 9
<211> LENGTH: 16
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(10)
<223> OTHER INFORMATION: n is a, c, g, or t

<400> SEQUENCE: 9
nnnnnnnnnn ctcgcc    16

<210> SEQ ID NO 10
<211> LENGTH: 16
<212> TYPE: DNA
<213> ORGANISM: Artificial sequence
<220> FEATURE:
<223> OTHER INFORMATION: Primer

<400> SEQUENCE: 10
gacgctcttc cgatct    16

<210> SEQ ID NO 11
<211> LENGTH: 14
<212> TYPE: DNA
<213> ORGANISM: Artificial sequence
<220> FEATURE:

```
<223> OTHER INFORMATION: Primer
<220> FEATURE:
<221> NAME/KEY: misc_feature
<222> LOCATION: (1)..(6)
<223> OTHER INFORMATION: n is a, c, g, or t

<400> SEQUENCE: 11
nnnnnntatg catg                                                       14

<210> SEQ ID NO 12
<211> LENGTH: 16
<212> TYPE: DNA
<213> ORGANISM: Artificial sequence
<220> FEATURE:
<223> OTHER INFORMATION: Primer

<400> SEQUENCE: 12
gacgctcttc cgatct                                                     16

<210> SEQ ID NO 13
<211> LENGTH: 14
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(6)
<223> OTHER INFORMATION: n is a, c, g, or t

<400> SEQUENCE: 13
nnnnnngcct cgcc                                                       14

<210> SEQ ID NO 14
<211> LENGTH: 16
<212> TYPE: DNA
<213> ORGANISM: Artificial sequence
<220> FEATURE:
<223> OTHER INFORMATION: Primer

<400> SEQUENCE: 14
gacgctcttc cgatct                                                     16

<210> SEQ ID NO 15
<211> LENGTH: 13
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(6)
<223> OTHER INFORMATION: n is a, c, g, or t

<400> SEQUENCE: 15
nnnnnnatgc atg                                                        13

<210> SEQ ID NO 16
<211> LENGTH: 16
<212> TYPE: DNA
<213> ORGANISM: Artificial sequence
<220> FEATURE:
<223> OTHER INFORMATION: Primer

<400> SEQUENCE: 16
gacgctcttc cgatct                                                     16
```

```
<210> SEQ ID NO 17
<211> LENGTH: 13
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(6)
<223> OTHER INFORMATION: n is a, c, g, or t

<400> SEQUENCE: 17
nnnnnncctc gcc                                                      13

<210> SEQ ID NO 18
<211> LENGTH: 16
<212> TYPE: DNA
<213> ORGANISM: Artificial sequence
<220> FEATURE:
<223> OTHER INFORMATION: Primer

<400> SEQUENCE: 18
gacgctcttc cgatct                                                   16

<210> SEQ ID NO 19
<211> LENGTH: 13
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(6)
<223> OTHER INFORMATION: n is a, c, g, or t

<400> SEQUENCE: 19
nnnnnncctc gcc                                                      13

<210> SEQ ID NO 20
<211> LENGTH: 16
<212> TYPE: DNA
<213> ORGANISM: Artificial sequence
<220> FEATURE:
<223> OTHER INFORMATION: Primer

<400> SEQUENCE: 20
gacgctcttc cgatct                                                   16

<210> SEQ ID NO 21
<211> LENGTH: 13
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(6)
<223> OTHER INFORMATION: n is a, c, g, or t

<400> SEQUENCE: 21
nnnnnngcct cgc                                                      13

<210> SEQ ID NO 22
<211> LENGTH: 36
<212> TYPE: DNA
<213> ORGANISM: Artificial sequence
<220> FEATURE:
<223> OTHER INFORMATION: Primer
<220> FEATURE:
```

-continued

<221> NAME/KEY: misc_feature
<222> LOCATION: (21)..(30)
<223> OTHER INFORMATION: n is a, c, g, or t

<400> SEQUENCE: 22
ctgaaccctt gtcgccattc nnnnnnnnnn cctccg        36

<210> SEQ ID NO 23
<211> LENGTH: 36
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(30)
<223> OTHER INFORMATION: n is a, c, g, or t

<400> SEQUENCE: 23
ctgaaccctt gtcgccattc nnnnnnnnnn gccgcc        36

<210> SEQ ID NO 24
<211> LENGTH: 34
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(26)
<223> OTHER INFORMATION: n is a, c, g, or t

<400> SEQUENCE: 24
acccttgtcg ccattcgata nnnnnntcat catg        34

<210> SEQ ID NO 25
<211> LENGTH: 34
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(26)
<223> OTHER INFORMATION: n is a, c, g, or t

<400> SEQUENCE: 25
acccttgtcg ccattcgata nnnnnntttg ttcc        34

<210> SEQ ID NO 26
<211> LENGTH: 33
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(26)
<223> OTHER INFORMATION: n is a, c, g, or t

<400> SEQUENCE: 26
acccttgtcg ccattcgata nnnnnncatc atg        33

<210> SEQ ID NO 27
<211> LENGTH: 33
<212> TYPE: DNA
<213> ORGANISM: Artificial sequence
<220> FEATURE:
<223> OTHER INFORMATION: Primer

```
<220> FEATURE:
<221> NAME/KEY: misc_feature
<222> LOCATION: (21)..(26)
<223> OTHER INFORMATION: n is a, c, g, or t

<400> SEQUENCE: 27
acccttgtcg ccattcgata nnnnnngcct cgc                              33

<210> SEQ ID NO 28
<211> LENGTH: 33
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(26)
<223> OTHER INFORMATION: n is a, c, g, or t

<400> SEQUENCE: 28
acccttgtcg ccattcgata nnnnnnttgt tcc                              33

<210> SEQ ID NO 29
<211> LENGTH: 33
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(26)
<223> OTHER INFORMATION: n is a, c, g, or t

<400> SEQUENCE: 29
acccttgtcg ccattcgata nnnnnnttgt tcc                              33
```

METHOD FOR GENOME COMPLEXITY REDUCTION AND POLYMORPHISM DETECTION

REFERENCE TO RELATED APPLICATIONS

This application is a continuation of U.S. application Ser. No. 13/535,190, filed Jun. 27, 2012 (pending), which claims the benefit of United States Provisional Application Nos. 61/571,472, filed Jun. 27, 2011, and 61/555,711, filed Nov. 4, 2011, and are herein incorporated by reference in their entirety.

INCORPORATION OF SEQUENCE LISTING

The sequence listing that is contained in the file named "UFFL012US_ST25.txt," which is 7 kilobytes as measured in Microsoft Windows operating system and was created on Jun. 27, 2012, is filed electronically herewith and incorporated herein by reference.

FIELD OF THE INVENTION

The invention relates generally to the fields of molecular biology and genetics. More particularly, the invention relates to DNA sequencing and genotyping.

BACKGROUND OF THE INVENTION

Extensive effort has been dedicated to genotyping human, plant, and animal populations to uncover genetic relationships and to identify genes that regulate clinical and agricultural traits, among many other uses. Current methods are costly and rely on large numbers of individuals. Technologies are needed to produce a reduced representation of the genome for sequencing and DNA polymorphism detection.

BRIEF SUMMARY OF THE INVENTION

In one aspect, the invention provides methods to produce a reduced representation of a genome for sequencing and DNA polymorphism detection comprising the steps of: (a) amplifying regions of a genome by polymerase chain reaction (PCR) using a first oligonucleotide primer set to produce a first nucleic acid product, wherein one of the primers of the first primer set comprises, starting from the 3' end: (i) a specific sequence at the 3' end of said primer wherein said specific sequence binds to unique target regions of said genome; (ii) a sequence that binds to all possible sequence combinations in the genome, which may, in certain embodiments, be a degenerate or universal nucleotide sequence; and (iii) a tail sequence that is complementary to a sequence of an oligonucleotide primer used in step (c) of said method; (b) normalizing the nucleic acid product of step (a) by contacting it with a duplex-specific nuclease for an effective amount of time to digest the most abundant double-stranded nucleic acid of step (a); and (c) amplifying by PCR the normalized nucleic acid product of step (b) using a second oligonucleotide primer set to produce a second nucleic acid product having a linker sequence, wherein a primer of said second primer set comprises, starting from the 5' end: (i) a linker sequence that is designed to support the binding of a DNA molecule to a surface; and (ii) a sequence complementary to said tail sequence of said primer of step (a), and wherein the nucleic acid product of step (c) represents a reduced representation of said genome.

In an embodiment of the present invention, the first oligonucleotide primer comprises a barcode sequence. In another embodiment, the specific sequence of the first oligonucleotide primer comprises between about 5 to about 10 nucleotides, and may include about 5, 6, 7, 8, 9, or 10 nucleotides. In another embodiment, the specific sequence of the first oligonucleotide primer comprises 6 nucleotides. In other embodiments of the invention, the degenerate sequence of the first oligonucleotide primer comprises between about 5 to about 15 nucleotides and may include about 5, 6, 7, 8, 9, 10, 11, 12, 13, 14, or 15 nucleotides. In still another embodiment, the degenerate sequence of the first oligonucleotide primer comprises 10 nucleotides.

In another embodiment, the invention provides for the use of a universal nucleotide sequence comprising between about 5 to about 15 nucleotides instead of degenerate sequences. Other embodiments provide a number of amplification cycles of PCR between about 15 to about 25 cycles. In another embodiment, the duplex-specific nuclease is from kamchatka crab. In still another embodiment, the duplex-specific nuclease is contacted with nucleic acid product of step (a) for about 2 to about 8 hours. In another embodiment, the nucleic acid product of step (c) is sequenced. In another embodiment, reduced representations of multiple genomes are produced. In still another embodiment, steps (b) and (c) comprise multiplexing multiple samples.

In another aspect, the invention provides an oligonucleotide primer comprising, starting from the 3' end: (i) a specific sequence at the 3' end of said primer, wherein said specific sequence binds to unique target regions of a genome; (ii) a sequence that binds to all possible sequence combinations in the genome, which may, in certain embodiments, be a degenerate or universal nucleotide sequence; and (iii) a tail sequence that is complementary to a sequence of an oligonucleotide primer used in step (c); or a second oligonucleotide primer, comprising, starting from the 5' end: (i) a linker sequence designed to support the binding of a DNA molecule to a surface; and (ii) a sequence complementary to the tail sequence of the primer in step (a).

In an embodiment of the present invention, the first oligonucleotide primer is classified as a barcode sequence. In another embodiment, the specific sequence of the first oligonucleotide primer comprises between about 5 to about 10 nucleotides, and may include about 5, 6, 7, 8, 9, or 10 nucleotides. In another embodiment, the specific sequence of the first oligonucleotide primer comprises 6 nucleotides. In another embodiments of the invention, the degenerate sequence of the first oligonucleotide primer comprises between about 5 to about 15 nucleotides and may include about 5, 6, 7, 8, 9, 10, 11, 12, 13, 14, or 15 nucleotides. In still another embodiment, the degenerate sequence of the first oligonucleotide primer comprises 10 nucleotides. The invention also provides for the use of a universal nucleotide sequence comprising between about 5 to about 15 nucleotides instead of degenerate sequences.

The invention also provides methods to produce a reduced representation of a genome for sequencing and DNA polymorphism detection comprising the steps of: (a) amplifying by polymerase chain reaction (PCR) regions of said genome using a single oligonucleotide primer set, wherein said oligonucleotide primer set results in the addition of a linker sequence; and (b) normalizing the nucleic acid product of step (a) by contacting it with a duplex-specific nuclease for an effective amount of time to digest the most abundant double-stranded nucleic acid of step (a); wherein the nucleic acid product of said method represents a reduced representation of said genome.

In one embodiment, a primer of the single oligonucleotide primer set comprises, starting from the 3' end: (i) a specific sequence that binds to unique target regions of the genome; (ii) a sequence that binds to all possible sequence combinations in the genome, which may be a degenerate or universal nucleotide sequence; and (iii) a tail sequence containing a linker sequence that is designed to support the binding of a DNA molecule to a surface for sequencing.

In an embodiment of the present invention, the oligonucleotide primer comprises a barcode sequence. In another embodiment, the specific sequence of the oligonucleotide primer comprises between about 5 to about 10 nucleotides, and may include about 5, 6, 7, 8, 9, or 10 nucleotides. In another embodiment, the specific sequence of the oligonucleotide primer comprises 6 nucleotides. In another embodiments of the invention, the degenerate sequence of the oligonucleotide primer comprises between about 5 to about 15 nucleotides and may include about 5, 6, 7, 8, 9, 10, 11, 12, 13, 14, or 15 nucleotides. In still another embodiment, the degenerate sequence of the oligonucleotide primer comprises 10 nucleotides.

The invention also provides for the use of a universal nucleotide sequence comprising between about 5 to about 15 nucleotides instead of degenerate sequences. Other embodiments provide a number of amplification cycles of PCR between about 15 to about 25 cycles. In another embodiment, the duplex-specific nuclease is from kamchatka crab. In still another embodiment, the duplex-specific nuclease is contacted with nucleic acid product of step (a) for about 2 to about 8 hours. In another embodiment, the nucleic acid product of step (c) is sequenced. In another embodiment, reduced representations of multiple genomes are produced. In still another embodiment, steps (b) and (c) comprise multiplexing multiple samples.

In another aspect, the invention provides a kit comprising in one or more containers one or more oligonucleotide primers as described herein. In an embodiment, the kit comprises instructions or packaging materials that describe how to use the one or more oligonucleotide primers in a method to produce a reduced representation of a genome. In further embodiments, the kit further comprises a duplex-specific nuclease. In a still further embodiment, said duplex-specific nuclease is from kamchatka crab.

In a further aspect, the invention comprises a method of obtaining a genotype of an individual comprising performing the above two-step PCR method and sequencing the second nucleic acid product or performing the above single PCR method and sequencing the resulting nucleic acid product. In another embodiment, the method of obtaining a genotype of an individual further comprises comparing the genotype of the individual to a reference genotype.

BRIEF DESCRIPTION OF THE FIGURES

FIG. 5: Shows annealing of the oligonucleotide used in PCR II (SEQ ID NO:1) to the normalized product of PCR I (SEQ ID NO:5).

BRIEF DESCRIPTION OF THE SEQUENCES

SEQ ID NO:1—Shows an example of a linker sequence that can be used for sequencing in an Illumina Genome Analyzer IIx. The linker sequence supports the binding of the DNA molecule to a flow-cell, bead, or any other surface to which fragments to be sequenced are anchored.

SEQ ID NO:2—Shows an example of a sequence complementary to the sequencing primer that can be used for sequencing in an Illumina Genome Analyzer IIx.

SEQ ID NO:3—Shows the complete sequence of SEQ ID NO:1 and 2.

Figure 2:
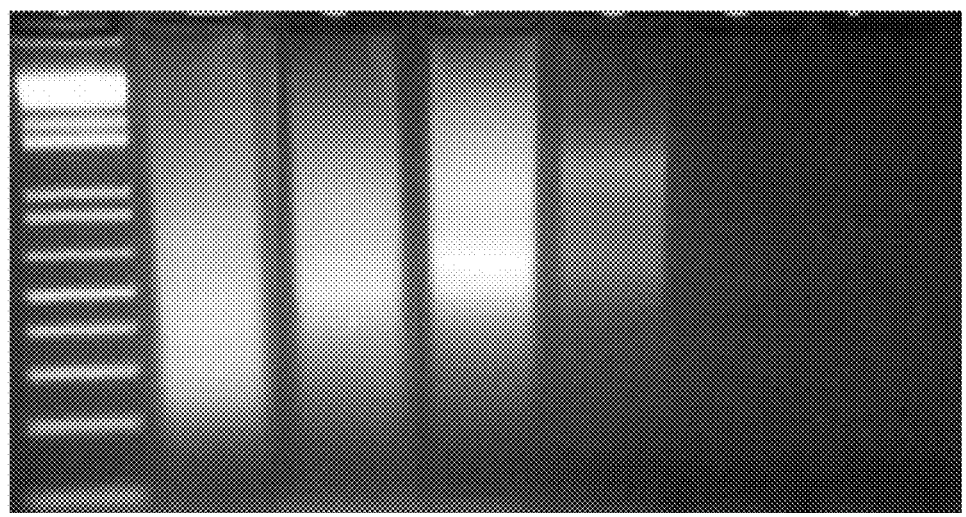
FIG. 2: Shows PCR I results using oligonucleotide primers with different numbers of degenerate nucleotides used in the degenerate sequence. Lanes represent PCR I amplification using primers with a degenerate sequence of 10 (lanes 2-3), 15 (lanes 4-5) and 20 (lanes 6-7) bases. For each number of degenerate bases tested, PCR conditions were as described in Example 6 as condition A (first lane) and condition B (second lane). Lane 1 is a 100-bp ladder.

SEQ ID NO:4—Shows the primer sequence as described in Example 1 (FIG. 2).

SEQ ID NO:5—Corresponds to the normalized product of PCR I (FIG. 5).

SEQ ID NO:6, 8, 10, 12, 14, 16, 18, and 20—correspond to the tail sequence (5' to 3') for primer A used in PCR I, for RAPID1-8, respectively.

SEQ ID NO:7, 9, 11, 13, 15, 17, 19, and 21—correspond to the degenerate sequence plus the specific sequence (5' to 3') for primer A used in PCR I, for RAPID1-8, respectively.

SEQ ID NO:22-29—correspond to the sequence (5' to 3') for primer B used in PCR I, for RAPID1-8, respectively.

DETAILED DESCRIPTION OF THE INVENTION

The invention provides methods and materials to produce a reduced representation of a genome for sequencing and DNA polymorphism detection. A method of the present invention uses a two-step PCR, intercalated by a normalization step. Methods for performing PCR and sequencing are known in the art. PCR as described herein may comprise additional reagents or steps to provide optimum amplification. Methods of optimization of PCR and sequencing are also known and are additionally described in the examples below. In one embodiment, the first PCR begins with the amplification of regions in the genome with oligonucleotide primers that contain a specific sequence in the 3' end, followed by a degenerate or universal nucleotide sequence, and then a tail sequence that is complementary to the oligonucleotide primer used in the second PCR. Optionally, the oligonucleotide primers can comprise a barcode sequence between the degenerate/universal nucleotide sequence and the tail sequence. In one embodiment, the specific sequence is about 5 to about 10 nucleotides and may include 5, 6, 7, 8, 9, or 10 nucleotides, and the degenerate sequence is about 5 to about 15 nucleotides, and may include 5, 6, 7, 8, 9, 10, 11, 12, 13, 14, or 15 nucleotides. In other embodiments, the specific sequence is 6 nucleotides and the degenerate sequence is 10 nucleotides. In another embodiment, a universal nucleotide sequence is used, instead of a degenerate oligonucleotide. Before the second PCR is performed, digestion with a duplex-specific nuclease (DSN) may be carried out to reduce representation of overly abundant nucleic acid fragments. Following DSN digestion, a second PCR may be carried out on the DSN-digested nucleic acid. In the second PCR, linkers that allow immediate sequencing in advanced DNA sequencers are incorporated into the oligonucleotide primers used in the PCR, resulting in a nucleic acid product containing a linker sequence. In one embodiment, the oligonucleotide primers used in the second PCR comprise a linker sequence at the 5' end that is designed to support binding of nucleic acid to a surface, followed by a sequence that is complementary to the tail sequence of the primers used in the first PCR. Both the normalization and the second PCR can be done by multiplexing multiple samples. In one embodiment, sequencing of the amplified nucleic acid products is performed following the second PCR.

Figure 1A:
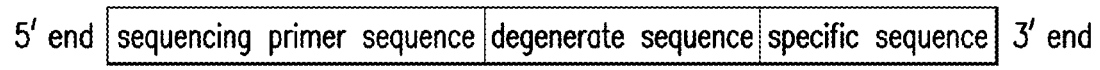
FIG. 1A: Shows a PCR I oligonucleotide primer composition.
Figure 1B:
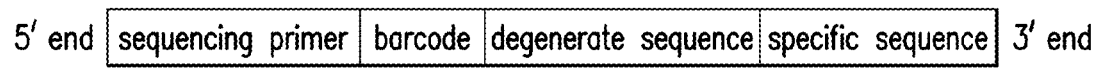
FIG. 1B: Shows a PCR I oligonucleotide primer composition containing a sequence barcode.

The invention also provides oligonucleotides that can be used in the methods of the present invention. In one embodiment, an oligonucleotide for the first PCR may comprise: (a) a specific sequence that binds to unique target regions of the genome being analyzed, (b) a degenerate sequence that binds to all possible sequence combinations in the genome, and (c) a sequence for annealing of a sequencing primer (FIG. 1A). In addition, (d) a barcode sequence, which is a sequence defined by the user for each sample, can optionally be included between (b) and (c) to permit sequencing of multiple samples in parallel and the posterior separation of their sequencing data (FIG. 1B). In one embodiment, the specific sequence is about 5 to about 10 nucleotides and may include 5, 6, 7, 8, 9, or 10 nucleotides, and the degenerate sequence is about 5 to about 15 nucleotides, and may include 5, 6, 7, 8, 9, 10, 11, 12, 13, 14, or 15 nucleotides. Alternatively, universal bases can replace the degenerate sequence. Embodiments of oligonucleotides for the first PCR are shown in Table 1.

In an embodiment, an oligonucleotide for the second PCR may comprise: (a) a linker sequence designed to support the binding of the DNA molecule to a flow-cell, bead, or any other surface to which fragments to be sequenced are anchored, such surfaces which are well known in the art, and (b) a sequence complementary to the sequencing primer described previously. In another embodiment, in the case of sequencing in an IIIumina Genome Analyzer IIx, a linker sequence (a) that can be used corresponds to: 5'-AATGA-TACGGCGACCACCGAGATCT-3' (SEQ ID NO:1), and sequence (b) that can be used is 5'-ACACTCTTTCCCTA-CACGACGCTCTTCCGATCT-3' (SEQ ID NO:2). Therefore, the complete sequence is:

(SEQ ID NO: 3)
5'-AATGATACGGCGACCACCGAGATCTACACTCTTTCCCTACACGACGC

TCTTCCGATCT-3'.

The invention further provides methods and materials to produce a reduced representation of a genome for sequencing and DNA polymorphism detection using a single PCR amplification. The single-PCR method comprises the steps of: (a) amplifying by polymerase chain reaction (PCR) regions of said genome using a first oligonucleotide primer set, in which a primer of the oligonucleotide primer set comprises, starting from the 3' end: (i) a specific sequence that binds to unique target regions of the genome; (ii) a degenerate or universal nucleotide sequence, (iii) a sequence that is designed for annealing of a sequencing primer and (iv) a linker sequence that is designed to support the binding of a DNA molecule to a surface; and (b) normalizing the nucleic acid product of step (a) by contacting it with a duplex-specific nuclease for an effective amount of time to digest the most abundant double-stranded nucleic acid of step (a); wherein the nucleic acid product of the method as described herein represents a reduced representation of the genome. This method employs a single PCR in which a single primer set as this described above is incorporated.

The invention also provides kits comprising in one or more containers, one or more oligonucleotide of the invention. In one embodiment, a kit of the invention includes one or more other components, adjuncts, or adjuvants as described herein. In another embodiment, a kit of the invention includes instructions or packaging materials that describe how to use an oligonucleotide or component of the invention. Containers of the kit can be of any suitable material, e.g., glass, plastic, metal, etc., and of any suitable size, shape, or configuration. In one embodiment, an oligonucleotide of the invention is provided in the kit as a solid, such as powder or lyophilized form. In another embodiment, an oligonucleotide of the invention is provided in the kit as a liquid or solution.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

EXAMPLES

Example 1

PCR I—Amplification of Genomic DNA Using a Degenerate or Universal Oligonucleotide Primer In this example, two PCR steps are utilized (PCR I and PCR II). The aim of PCR I is to amplify a set of regions in the genome that are flanked by specific sequences defined by an oligonucleotide primer. After amplification, these regions will represent a reduced representation of the genome, to which linkers are added in PCR II, followed by sequencing and polymorphism genotyping.

The first step of reducing the genome complexity occurs through PCR amplification using an oligonucleotide primer. The oligonucleotide primers contain three components, starting from the 3' end: (a) a specific sequence that binds to unique target regions of the genome; (b) a degenerate or universal sequence that binds to all possible sequence combinations in the genome; and (c) a tail sequence for annealing of a sequencing primer (referred to as a sequencing primer sequence or sequencing primer in FIGS. 1A and B) (FIG. 1A). In addition, (d) a barcode sequence can be included between (b) and (c) to permit sequencing of multiple samples in parallel and the posterior separation of their sequencing data (FIG. 1B).

The specific sequence (a) defines the starting positions in the genome, from where amplification by the DNA polymerase will occur. Selection of the specific sequence (a) depends on both the number of fragments that one desires to sample in the genome and their distribution. For example, selection of a specific sequence with 6 nucleotides (nt) typically yields a larger number of fragments than a specific sequence with 10 nt, which is likely anneal to the genome less frequently (see Example 2). Certain sequences are also likely to amplify fragments that are more consistently distributed in the genome than others. Therefore, if a reference genome is available for the organism of interest, this distribution can be estimated to guide the selection of the most appropriate specific sequence.

Of note, two or more degenerate oligonucleotides that differ only in their specific sequence may be used in combination in a single PCR, providing more flexibility in the regions of the genome that will be amplified. To demonstrate this, one degenerate oligonucleotide primer was synthesized with the sequence 5'-CTCGCC-3' (FIG. 2) and another synthesized with the sequence 5'-GCCGCC-3'. This combination of primers amplified approximately 30,000 regions of the *Eucalyptus grandis* genome in a range of 200-600 base pairs, based on predicted and observed number of fragments generated after PCR amplification and sequencing.

The degenerate or universal sequence (b) provides stability to the oligonucleotide primer when it anneals to the genome during PCR, potentially allowing the use of more stringent PCR conditions and thus limiting non-specific amplification. Different numbers of degenerate bases (10, 15, and 20) in the degenerate sequence were tested (see Example 2). Alternatively, universal bases may be used instead of degenerate bases. FIG. 2 shows a degenerate sequence containing 10 degenerate nt.

The sequencing primer sequence (c) is defined by the user, depending on the primer used for initiation of DNA polymerization in the sequencing reaction. In the example provided (FIG. 2), the primer sequence is defined by the sequence 5'-ACACGACGCTCTTCCGATCT-3' (SEQ ID NO:4).

A barcode sequence (d) is defined by the user, depending on the number of samples that one wishes to multiplex during sequencing. In the example provided (FIG. 2), the barcode sequence is defined by the sequence 5'-ACTG-3'.

Unless described differently below, the reaction conditions for PCR I were as follows: 60 ng of genomic DNA, 0.2 mM dNTPs, 2 units of Taq DNA polymerase (Platinum DNA Polymerase High-fidelity), 0.5 µM of the oligonucleotide primer, and 3 µM of the 10×DNA polymerase buffer, in a 30 µL reaction.

Example 2

Optimization of Oligonucleotide Primer Properties for PCR I

The oligonucleotide primer properties that were defined are (a) the number of degenerate (N) bases to be used in the degenerate sequence and (b) the number and type (i.e., A, C, G, or T) of bases to be used in the specific sequence.

Number of Bases in the Degenerate Sequence.

As each additional degenerate base is added to the oligonucleotide primer, the concentration for a given primer composition decreases by ¼ relative to the total primer concentration (assuming that each nucleotide—A, C, G and T—is added in an equimolar amount in the degenerate position). Therefore, PCR amplification is expected to decrease as additional degenerated bases are added, as fewer primers will be available to amplify a given product. We tested PCR amplification using 10, 15, and 20 degenerate bases using standard PCR conditions (see below). The primers tested are described in Table 1. As anticipated, a significant decrease in the amount of product synthesized in the PCR I was observed when a higher number of degenerate bases were utilized (FIG. 2). While both PCR conditions described below (see Example 3) produce clear amplification results when 10 degenerate bases are used, amplification is less pronounced with 15, and absent with 20 degenerate bases. In order to support further optimization of PCR I, regardless of cycle annealing and extension condition, we selected 10 as the maximum number of degenerate bases to be included in the degenerate sequence.

Composition of the Bases in the Degenerate Sequence.

Alternatively, instead of synthesizing a degenerate sequence containing one of the four bases in a proportion of ¼ at any position, a universal base may be used (e.g., inosine) which binds to any nucleotide in all positions.

Number and Type (i.e., A, C, G, or T) of Bases to be Used in the Specific Sequence.

Figure 3A:
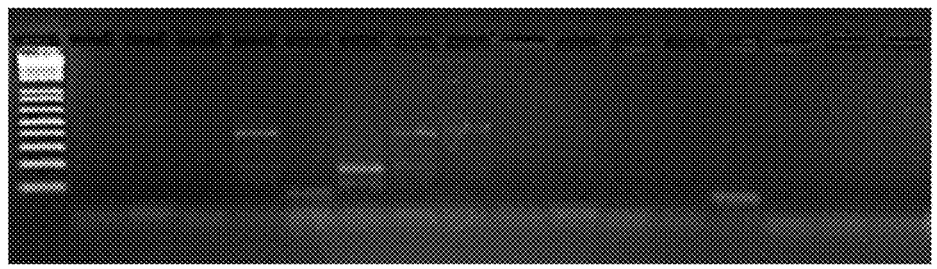
FIG. 3A: Shows PCR I results using oligonucleotide primers with different number of nucleotides and nucleotide composition in the specific sequence. PCR conditions are as described in Example 6 (condition A). PCR products in lanes 2-9 were amplified by oligonucleotide primers described in Table 1 (lane 2=RAPID1, lane 3=RAPID2, lane 4=RAPID3, lane 5=RAPID4, lane 6=RAPID5, lane 7=RAPID6, lane 8=RAPID7, and lane 9=RAPID8). PCR products from lanes 10-17 represent amplifications using the same oligonucleotide primers, without DNA (negative control). Lane 1 is a 100-bp ladder.
Figure 3B:
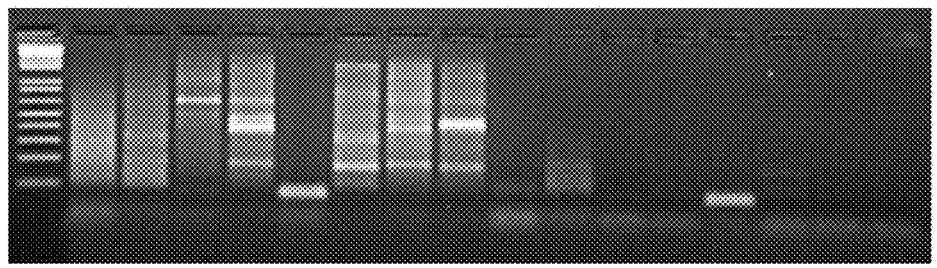
FIG. 3B: Shows PCR I results using oligonucleotide primers with different number of nucleotides and nucleotide composition in the specific sequence. PCR conditions are as described in Example 6 (condition B). PCR products in lanes 2-9 were amplified by oligonucleotide primers described in Table 1 (lane 2=RAPID1, lane 3=RAPID2, lane 4=RAPID3, lane 5=RAPID4, lane 6=RAPID5, lane 7=RAPID6, lane 8=RAPID7, and lane 9=RAPID8). PCR products from lanes 10-17 represent amplifications using the same oligonucleotide primers, without DNA (negative control). Lane 1 is a 100-bp ladder.

In order to evaluate the impact of using different number of nucleotides and composition in the amplification of genomic products, we tested the use of 6, 7, and 8 nucleotides in the specific sequence of the oligonucleotide primer. The primers tested are described in Table 1. Overall, the use of 7 and 8 nucleotides lead to a reduction in product complexity, recognized by the observation of discrete bands in agarose gel (FIG. 3). On the contrary, the use of oligonucleotide primers with only 6 nucleotides is sufficiently complex to generate a smear, with no clearly visible banding pattern. Therefore, to limit the over-amplification of few unique products, we selected the use of primers with 6 nucleotides in the specific sequence.

The amplification profile depends on the specific sequence of the oligonucleotide primer, as well as the genome complexity and composition. Therefore, the selection of oligonucleotide primers has to be determined for each targeted species.

observed, depending on the primer combination used in PCR I. Note that the number of cycles has to be determined for each primer combination used in PCR I.

TABLE 1

PCR I oligonucleotide primers of different lengths and nucleotide composition used in the specific sequence (N = degenerate nucleotide). Primer combinations RAPID1-8 of Primer A comprise a barcode sequence between the tail sequence and the degenerate sequence + specific sequence.

| | Sequence (5'-3') Primer A | | | Sequence (5'-3') Primer B | |
|---|---|---|---|---|---|
| Primer Combination | Tail Sequence | SEQ ID NO: | Degenerate Sequence + Specific Sequence | SEQ ID NO: | Primer | SEQ ID NO: |
| RAPID1 | ACACGACGCTCTTCCGATCT | 6 | NNNNNNNNNNGCGAGG | 7 | CTGAACCCTTGTCGCCATTCNNNNNNNNNNCCTCCG | 22 |
| RAPID2 | ACACGACGCTCTTCCGATCT | 8 | NNNNNNNNNNCTCGCC | 9 | CTGAACCCTTGTCGCCATTCNNNNNNNNNNGCCGCC | 23 |
| RAPID3 | GACGCTCTTCCGATCT | 10 | NNNNNNTATGCATG | 11 | ACCCTTGTCGCCATTCGATANNNNNNTCATCATG | 24 |
| RAPID4 | GACGCTCTTCCGATCT | 12 | NNNNNNGCCTCGCC | 13 | ACCCTTGTCGCCATTCGATANNNNNNNTTTGTTCC | 25 |
| RAPID5 | GACGCTCTTCCGATCT | 14 | NNNNNNATGCATG | 15 | ACCCTTGTCGCCATTCGATANNNNNNCATCATG | 26 |
| RAPID6 | GACGCTCTTCCGATCT | 16 | NNNNNNCCTCGCC | 17 | ACCCTTGTCGCCATTCGATANNNNNNGCCTCGC | 27 |
| RAPID7 | GACGCTCTTCCGATCT | 18 | NNNNNNCCTCGCC | 19 | ACCCTTGTCGCCATTCGATANNNNNNTTGTTCC | 28 |
| RAPID8 | GACGCTCTTCCGATCT | 20 | NNNNNGCCTCGC | 21 | ACCCTTGTCGCCATTCGATANNNNNNTTGTTCC | 29 |

Example 3

Optimization of PCR Cycle Annealing and Extension Conditions for PCR I

Two alternative strategies were tested regarding the PCR annealing and extension conditions in PCR I. Condition A involved a PCR profile consisting of 30 cycles of 94° C. for 2 min, 45° C. for 1 min, and 68° C. for 0.5 min, and a final step at 68° C. for 5 min. Alternatively, condition B was used, consisting of 94° C. for 2 min, followed by 5 cycles of 94° C. for 2 min, 45° C. for 1 min, ramp 2 min to 68° C., and 68° C. for 0.5 min; then 25 cycles of 94° C. for 2 min, 62° C. for 1 min, and 68° C. for 0.5 min, and a final step at 68° C. for 5 min.

Example 4

Optimization of Number of PCR Cycles for PCR I

Figure 4:
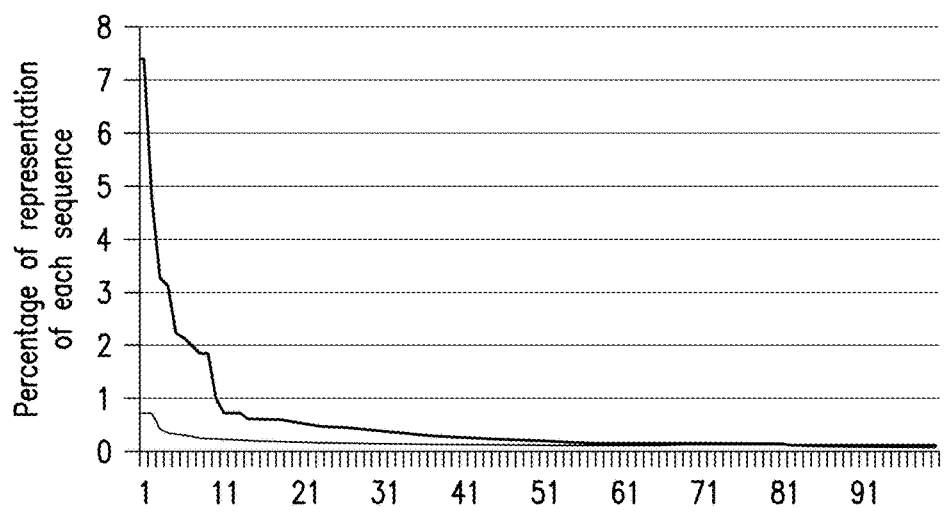
FIG. 4: Shows a representation (% of total number of sequencing reads) of each of the 100 most abundant sequences observed (X-axis), after samples were treated (light grey) or not treated (dark grey) with the duplex-specific nuclease (DSN) enzyme.

Methods aimed at PCR amplifying large numbers of regions in the genome for sequencing and genotyping have previously been proposed, but are hampered by over-amplification of few specific targets in the genome (Jordan et al., Proc. Natl. Acad. Sci. U.S.A. 99:2942-2947, 2002). As a result, there is an over-representation of a subset of genomic regions among sequencing reads, and the lack of representation of others. This over-amplification is exacerbated by increasing the number of PCR cycles, because fragment amplification by PCR increases exponentially with each additional cycle. Therefore, in PCR I, we favor using the lowest possible number of cycles in order to minimize the over-amplification of specific regions of the genome. To determine the adequate number of PCR cycles for each set of primers used in PCR I, the synthesis of products generated at each cycle was followed, using quantitative RT-PCR (FIG. 4). The exponential amplification at 15-25 cycles was Example 5

Normalization of PCR Products

Regardless of the protocol adopted in PCR I, the over-representation of certain regions of the genome among sequencing reads can only be minimized by manipulating the reaction conditions (particularly, the number of PCR cycles), but not entirely eliminated. Therefore, alternative approaches that reduce amplification bias are critical for the feasibility of genotyping by sequencing products derived from PCR I. The present invention is innovative over the art, for instance, in the introduction of a normalization step using a duplex-specific nuclease (DSN), aimed at minimizing the over-representation of specific fragments among sequencing reads. The normalization step involves the denaturation of PCR I products, and their subsequent renaturation, followed by degradation of the most abundant double-stranded DNA fraction by a duplex-specific nuclease (DSN). In order to evaluate the effect of a DSN treatment in reducing over-representation of products among sequenced fragments, we carried out PCR I with the conditions described below. Briefly, 60 ng of genomic DNA were combined with the 0.2 mM dNTPs, 2 units of Taq DNA polymerase (Platinum DNA Polymerase High-fidelity), 0.5 µM of the oligonucleotide primer, and 3 µM of the 10×DNA polymerase buffer, in a 30 ΣL reaction. The PCR profile consisted of 94° C. for 2 min, followed by 5 cycles of 94° C. for 2 min, 45° C. for 1 min, ramp 2 min to 68° C., and 68° C. for 0.5 min; then 18 cycles of 94° C. for 2 min, 62° C. for 1 min, and 68° C. for 0.5 min, and a final step at 68° C. for 5 min. PCR products were then purified and eluted in 10 uL using standard procedures (Qiagen Mini-Elute column). Next, 3 µL of each purified PCR product were (1) used in PCR II (described below), or (2) treated with DSN prior to amplification in PCR II. For DSN treatment, the enzyme isolated from the kamchatka crab (Duplex-specific nuclease, Evrogen) was used, which exhibits a strong preference for double-stranded DNA as a substrate and is stable under elevated temperatures (Shagin et al., *Genome Res.* 12:1935-42, 2002). PCR I products were incubated for 5 hrs with ⅛ of a unit of DSN, following the manufacturer's protocol (Evrogen, Moscow, Russia). Normalized PCR products were then used in PCR II (protocol described below) and sequenced. After sequencing, the frequency of each of the 100 most common reads was compared to non-normalized products, to evaluate success of the procedure. As shown in FIG. 4, DSN enzyme treatment clearly reduced the representation of fragments that were overly abundant following PCR I. For this analysis, in which we used the RAPID2 primer combination (Table 1), lack of enzyme treatment results in 53% of sequencing reads being composed of the 100 most abundant fragments. With DSN treatment, the most common 100 sequences represented only 15% of the total reads. The most abundant fragment represented over 7% of the sequencing reads in the original conditions (i.e., no enzyme treatment), but was <1% after use of DSN (FIG. 4). Therefore, treatment of PCR I products with a duplex-specific nuclease is critical for reducing the over-representation of few PCR products among sequencing reads.

Example 6

PCR II—Incorporation of Linker Sequences

The present invention is further novel over the art by the introduction of a second PCR (PCR II) aimed at producing a reduced representation of the genome that is rapidly and cost-effectively prepared, and suitable for sequencing. Previously published methodologies have utilized similar approaches as the one described in Examples 1-5. for generating a reduced representation of the genome. In one study, Jordan et al. (*Natl. Acad. Sci. U.S.A.,* 99:2942-2947, 2002) generated reduced representations of the genome using an oligonucleotide primer containing a specific sequence in the 3' end, followed by degenerate nucleotides, and a sequence "tail" containing a restriction site. After PCR amplification, enzyme digestion of the restriction site was carried out, followed by ligation and cloning in *E. coli*. Cloned plasmids from transformed cells were then extracted and purified for sequencing. The approach introduced here eliminates the cloning step, so that in one simple PCR, samples are ready for sequencing. The procedure also avoids costly and time-consuming methods of library construction, typically required for preparation of samples for second-generation sequencing. Because reduced genome representations of each individual may be identified by a unique barcode introduced during the PCR I, multiple samples can be combined in a single PCR II, further lowering costs and increasing throughput of this approach.

Following PCR I and the normalization of PCR products, fragments can be sequenced in a variety of sequencing platforms. However, prior to sequencing, specific linker sequences are added to each end of the molecules. Such linker sequences are used for analysis in second-generation sequencers and are dependent on the sequencer platform. Generally, linker sequences have been added to reduced representations of the genome by restriction digestion, and ligation of adaptors containing the suitable sequence (Jordan et al., *Natl. Acad. Sci. U.S.A.,* 99:2942-2947, 2002). The process is simplified by the introduction of PCR II, where linkers are introduced by extension from overhanging primers. Essentially, PCR amplification occurs using an oligonucleotide primer that contains two components, starting from the 5' end: (a) a linker sequence designed to support the binding of the DNA molecule to a flow-cell, bead, or any other surface to which fragments to be sequenced are anchored, and (b) a sequence complementary to the sequencing primer described previously. In the case of sequencing in an Illumina Genome Analyzer IIx, linker sequence (a) corresponds to: 5'-AATGATACGGCGACCACCGA-GATCT-3' (SEQ ID NO:1), and sequence (b) is 5'-ACACTCTTTCCCTACACGACGCTCTTCCGATCT-3' (SEQ ID NO:2). Therefore, the complete sequence is:

(SEQ ID NO: 3)
5'-AATGATACGGCGACCACCGAGATCTACACTCTTTCCCTACACGACGC

TCTTCCGATCT-3'.

This primer anneals as described in FIG. 5 to the degenerate oligonucleotide primer used in PCR I.

The PCR conditions for incorporation of the linker sequence in PCR II were optimized to maximize the synthesis of products adequate for use in sequencing platforms (i.e., containing the linker), while minimizing the number of cycles required. Once again, the purpose of minimizing the number of cycles was to reduce the over-amplification of certain products favorably amplified in PCR I. In addition, dimers formed by the degenerate oligonucleotide primers used in PCR I are most likely to be amplified in PCR II because of their small size. Therefore, conditions that minimize their amplification are also critical.

PCR II included 0.2 mM dNTPs, 1 unit of Taq DNA polymerase (Platinum DNA Polymerase High-fidelity), 0.1 µM of the primer, and 5 µM of the 10×DNA polymerase buffer, in a 50 µL reaction. Ten microliters of purified product from PCR I were used in PCR II. The PCR profile consisted of 94° C. for 3 min, followed by cycles of 94° C. for 2 min, 57° C. for 0.5 min, and 68° C. for 1 min, and a final step at 68° C. for 10 min. The number of cycles was defined as described below.

Example 7

Optimization of Number of PCR Cycles for PCR II

Figure 6:
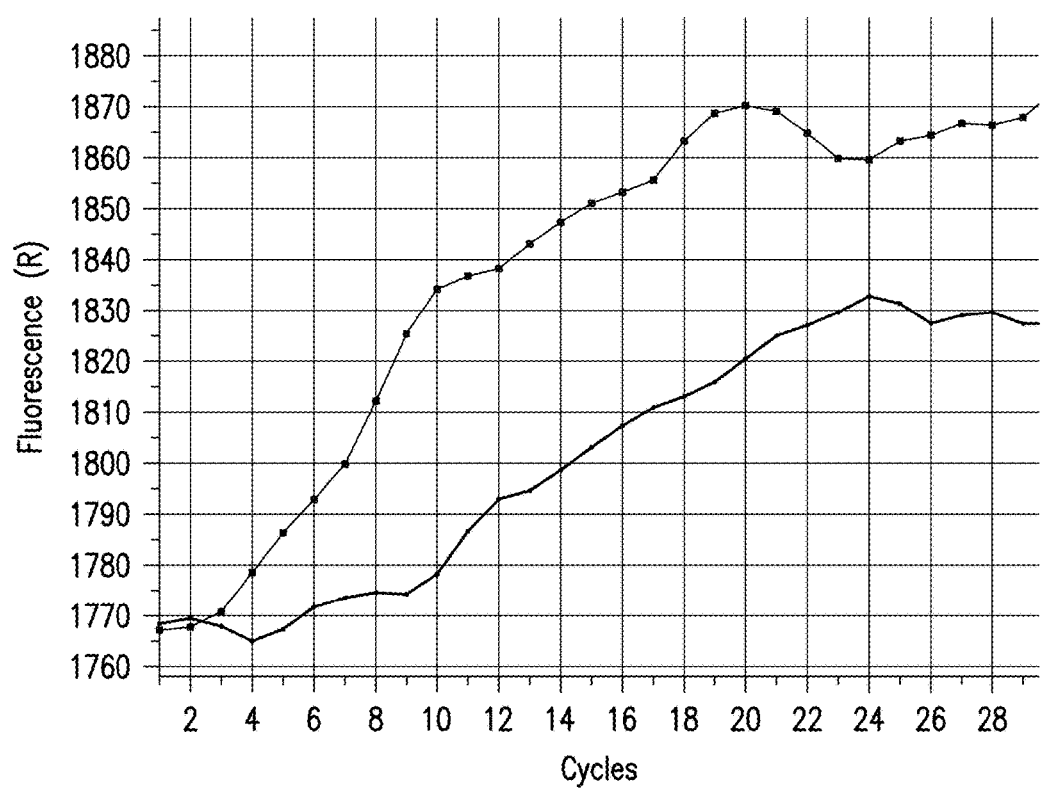
FIG. 6: Shows linker incorporation during PCR II, measured by qRT-PCR. The incorporation of linkers in the reaction containing genomic DNA (dark grey) increases exponentially after the $3^{rd}$ cycle. Linker incorporation in the negative control reaction (light grey) only occurs later (~$10^{th}$ cycle).

To evaluate the minimal number of cycles that are necessary for incorporation of adapters in PCR II, the synthesis of products was quantified by qRT-PCR, using the primer described in FIG. 5, and the reaction conditions described above. The qRT-PCR profile was also generated using a control reaction, to quantify the generation of primer dimers. The results indicate that 5-7 cycles adequately produce products containing the linker sequence while minimizing the generation of dimers. As the number of cycles increased, the quantity of dimers formed becomes significant and undesirable (FIG. 6). Analysis of sequencing data indicated that fewer than 1% of sequencing reads were derived from dimers.

Example 8

Production of a Reduced Representation of a Genome in a Single PCR

In this example, a single PCR would be utilized for production of a reduced representation of a genome. Using a single PCR would enable simultaneous amplification of a set of regions in the genome that are flanked by specific sequences defined by an oligonucleotide primer and attachment of linkers for DNA sequencing reactions. The oligonucleotide primers used in the single-PCR method would comprise one primer set, which would contain four components, starting from the 3' end: (a) a specific sequence that binds to unique target regions of the genome; (b) a degenerate or universal sequence that binds to all possible sequence combinations in the genome; (c) a sequence for annealing of a sequencing primer; and (d) a linker sequence that is designed to support the binding of a DNA molecule to a surface. In addition, (e) a barcode sequence can be included between (b) and (c) to permit sequencing of multiple samples in parallel and the posterior separation of their sequencing data.

Reaction conditions used for the single-PCR method would be as follows: 60 ng of genomic DNA, 0.2 mM dNTPs, 2 units of Taq DNA polymerase (Platinum DNA Polymerase High-fidelity), 0.5 µM of the oligonucleotide primer, and 3 µM of the 10×DNA polymerase buffer, in a 30 µL reaction. However, one of skill would recognize that these conditions would be able to be optimized, as well known in the art and described above to obtain the most efficient reaction, for instance limiting the over-amplification of a few specific targets while increasing the amplification of remaining sequences. After amplification the PCR product would then be contacted with DSN to normalize the amplification product. PCR product from the single-PCR reaction may then be sequenced or genotyped by known methods.

What is claimed is:

1. A method for producing a reduced representation of a genome, comprising the steps of:
   (a) amplifying by polymerase chain reaction (PCR) regions of the genome using a first oligonucleotide primer set to produce a first nucleic acid product;
   (b) normalizing the nucleic acid product of step (a) by contacting it with a duplex-specific nuclease for an effective amount of time to digest the most abundant double-stranded nucleic acid product of step (a); and
   (c) amplifying by PCR the normalized nucleic acid product of step (b) using a second oligonucleotide primer set to produce a second nucleic acid product having a linker sequence, wherein a primer of the second oligonucleotide primer set comprises said linker sequence; and
   wherein the nucleic acid product of step (c) represents a reduced representation of the genome.

2. The method of claim 1, wherein
   (A) a primer of the first primer set comprises, starting from the 3' end: (i) a specific sequence that binds to unique target regions of the genome; (ii) a sequence that binds to all possible sequence combinations in the genome; and (iii) a tail sequence; and
   (B) a primer of the second primer set comprises, starting from the 5' end: (i) a linker sequence that is designed to support the binding of a DNA molecule to a surface; and (ii) a sequence complementary to the tail sequence of the primer of step (A).

3. The method of claim 2, wherein said primer of said first oligonucleotide primer set further comprises a barcode sequence.

4. The method of claim 2, wherein said specific sequence of the primer of the first oligonucleotide primer set comprises between about 5 to about 10 nucleotides.

5. The method of claim 4, wherein said specific sequence comprises 6 nucleotides.

6. The method of claim 2, wherein the sequence that binds to all possible sequence combinations in the genome is a degenerate sequence.

7. The method of claim 6, wherein said degenerate sequence comprises between about 5 to about 15 nucleotides.

8. The method of claim 7, wherein the degenerate sequence comprises 10 nucleotides.

9. The method of claim 2, wherein the sequence that binds to all possible sequence combinations in the genome is a universal nucleotide sequence.

10. The method of claim 9, wherein the universal nucleotide sequence comprises between about 5 to about 15 nucleotides.

11. The method of claim 1, wherein the number of amplification cycles of PCR in step (a) is between about 15 to about 25.

12. The method of claim 1, wherein said duplex-specific nuclease is from kamchatka crab.

13. The method of claim 1, wherein the contacting of step (b) is for about 2 to about 8 hours.

14. The method of claim 1, further comprising sequencing the second nucleic acid product of step (c).

15. The method of claim 1, wherein reduced representations of multiple genomes are produced.

16. The method of claim 1, wherein steps (b) and (c) comprise multiplexing multiple samples.

17. A method for producing a reduced representation of a genome, comprising the steps of:
(a) amplifying by polymerase chain reaction (PCR) regions of said genome using a single oligonucleotide primer set, wherein a primer of the oligonucleotide primer set comprises a linker sequence, and said oligonucleotide primer set results in the addition of said linker sequence; and
(b) normalizing the nucleic acid product of step (a) by contacting it with a duplex-specific nuclease for an effective amount of time to digest the most abundant double-stranded nucleic acid of step (a);
wherein the nucleic acid product of said method represents a reduced representation of said genome.

18. The method of claim 17, wherein
a primer of the oligonucleotide primer set comprises, starting from the 3' end: (i) a specific sequence that binds to unique target regions of the genome; (ii) a sequence that binds to all possible sequence combinations in the genome; and (iii) a tail sequence containing said linker sequence that is designed to support the binding of a DNA molecule to a surface for sequencing.

19. The method of claim 18, wherein said primer of said oligonucleotide primer set further comprises a barcode sequence.

20. The method of claim 18, wherein said specific sequence of the primer of the oligonucleotide primer set comprises between about 5 to about 10 nucleotides.

21. The method of claim 20, wherein said specific sequence comprises 6 nucleotides.

22. The method of claim 18, wherein the sequence that binds to all possible sequence combinations in the genome is a degenerate sequence.

23. The method of claim 22, wherein said degenerate sequence comprises between about 5 to about 15 nucleotides.

24. The method of claim 23, wherein the degenerate sequence comprises 10 nucleotides.

25. The method of claim 18, wherein the sequence that binds to all possible sequence combinations in the genome is a universal nucleotide sequence.

26. The method of claim 25, wherein the universal nucleotide sequence comprises between about 5 to about 15 nucleotides.

27. The method of claim 17, wherein the number of amplification cycles of PCR in step (a) is between about 15 to about 25.

28. The method of claim 17, wherein said duplex-specific nuclease is from kamchatka crab.

29. The method of claim 17, wherein the contacting of step (b) is for about 2 to about 8 hours.

30. The method of claim 17, further comprising sequencing a resulting nucleic acid product.

31. The method of claim 17, wherein reduced representations of multiple genomes are produced.

32. The method of claim 17, wherein steps (b) and (c) comprise multiplexing multiple samples.

33. A method of obtaining a genotype of an individual comprising performing the method of claim 1 and sequencing the second nucleic acid product to obtain the genotype of said individual based on the DNA sequence of the second nucleic acid product.

34. The method of claim 33, further comprising comparing the genotype of the individual to a reference genotype.

35. A method of obtaining a genotype of an individual comprising performing the method of claim 17 and sequencing the resulting nucleic acid product to obtain the genotype of said individual.

36. The method of claim 35, further comprising comparing the genotype of the individual to a reference genotype.

* * * * *